(12) United States Patent
Ou-Yang

(10) Patent No.: US 8,426,348 B2
(45) Date of Patent: Apr. 23, 2013

(54) ANTIMICROBIAL LUBRICANT COMPOSITIONS

(75) Inventor: David Tien-Tung Ou-Yang, Woodbury, MN (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 321 days.

(21) Appl. No.: 12/436,404

(22) Filed: May 6, 2009

(65) Prior Publication Data

US 2010/0137379 A1  Jun. 3, 2010

Related U.S. Application Data

(60) Provisional application No. 61/118,988, filed on Dec. 1, 2008.

(51) Int. Cl.
  *C10M 125/18* (2006.01)
  *C10M 133/06* (2006.01)
  *C10M 169/02* (2006.01)

(52) U.S. Cl.
  USPC ............................ 508/547; 508/136; 508/150

(58) Field of Classification Search .................. 508/150, 508/136, 547
  See application file for complete search history.

(56) References Cited

U.S. PATENT DOCUMENTS

| | | | |
|---|---|---|---|
| 3,223,629 A | 12/1965 | Loeffler | |
| 4,339,336 A | 7/1982 | Hammond et al. | |
| 4,584,192 A | 4/1986 | Dell et al. | |
| 4,716,032 A | 12/1987 | Westfall et al. | |
| 4,915,934 A | 4/1990 | Tomlinson | |
| 4,925,668 A | 5/1990 | Khan et al. | |
| 5,023,082 A | 6/1991 | Friedman et al. | |
| 5,512,199 A | 4/1996 | Khan et al. | |
| 5,547,662 A | 8/1996 | Khan et al. | |
| 5,616,338 A | 4/1997 | Fox, Jr. et al. | |
| 5,861,440 A | 1/1999 | Gohla et al. | |
| 6,051,609 A | 4/2000 | Yu et al. | |
| 6,127,320 A | 10/2000 | van Ooij et al. | |
| 6,248,811 B1 | 6/2001 | Ottersbach et al. | |
| 6,337,357 B1 | 1/2002 | Fukunishi et al. | |
| 6,413,539 B1 | 7/2002 | Shalaby | |
| 6,488,942 B1 | 12/2002 | Ingemann | |
| 6,576,633 B1 * | 6/2003 | Young et al. | ............... 514/244 |
| 6,861,060 B1 | 3/2005 | Luriya et al. | |
| 6,896,889 B2 | 5/2005 | Chevalier et al. | |
| 7,198,800 B1 | 4/2007 | Ko | |
| 2001/0016589 A1 | 8/2001 | Modak et al. | |

(Continued)

FOREIGN PATENT DOCUMENTS

| | | |
|---|---|---|
| EP | 0 338 418 A1 | 4/1989 |
| EP | 0 379 271 A2 | 1/1990 |

(Continued)

*Primary Examiner* — Jim Goloboy
(74) *Attorney, Agent, or Firm* — Jeanne Lukasavage; Craig Metcalf; Kirton McConkie

(57) ABSTRACT

Antimicrobial lubricant compositions are disclosed. The antimicrobial lubricant compositions are particularly useful in providing antimicrobial capability to a wide-range of medical devices. The compositions include an oil lubricant. Representative lubricants may include polydimethyl siloxane, trifluoropropyl copolymer polysiloxane, and a copolymer of dimethylsiloxane and trifluoropropylmethylsiloxane. The compositions include rheology modifiers as necessary. The compositions also include antimicrobial agents, which may be selected from a wide array of agents. Representative antimicrobial agents include of aldehydes, anilides, biguanides, bis-phenols, quaternary ammonium compounds, cetyl pyridium chloride, cetrimide, alexidine, chlorhexidine diacetate, benzalkonium chloride, and o-phthalaldehyde.

17 Claims, 1 Drawing Sheet

U.S. PATENT DOCUMENTS

| | | |
|---|---|---|
| 2002/0028751 A1* | 3/2002 | Lokkesmoe et al. .......... 508/161 |
| 2002/0119111 A1 | 8/2002 | Kilgour et al. |
| 2002/0144705 A1 | 10/2002 | Brattesani et al. |
| 2003/0072781 A1 | 4/2003 | Pelerin |
| 2003/0119932 A1 | 6/2003 | Al-Akhdar et al. |
| 2003/0162839 A1 | 8/2003 | Symington et al. |
| 2004/0039349 A1 | 2/2004 | Modak et al. |
| 2004/0058829 A1* | 3/2004 | Hei et al. ...................... 508/208 |
| 2004/0234475 A1 | 11/2004 | Lannibois-Drean et al. |
| 2006/0165751 A1 | 7/2006 | Chudzik et al. |
| 2006/0239954 A1 | 10/2006 | Sancho |
| 2006/0258780 A1 | 11/2006 | Chaussade et al. |
| 2007/0112112 A1 | 5/2007 | Kerschner et al. |
| 2007/0112146 A1 | 5/2007 | Falk et al. |
| 2007/0160547 A1 | 7/2007 | Duffy et al. |
| 2007/0225179 A1* | 9/2007 | Schutz et al. ................ 508/207 |
| 2008/0075761 A1 | 3/2008 | Modak et al. |
| 2008/0161763 A1* | 7/2008 | Harding et al. ............... 604/265 |
| 2008/0182921 A1 | 7/2008 | Suh et al. |
| 2009/0114327 A1 | 5/2009 | Breunig |

FOREIGN PATENT DOCUMENTS

| | | |
|---|---|---|
| WO | 98/58690 | 12/1998 |
| WO | 9858989 | 12/1998 |
| WO | 99/32168 | 7/1999 |
| WO | 00/66189 | 11/2000 |
| WO | 2006/074666 A2 | 7/2006 |
| WO | WO 2006099358 A2 * | 9/2006 |
| WO | 2007/100653 A2 | 9/2007 |
| WO | 2007100776 A2 | 9/2007 |
| WO | 2008/014447 A2 | 1/2008 |
| WO | 2008132045 A2 | 11/2008 |

* cited by examiner

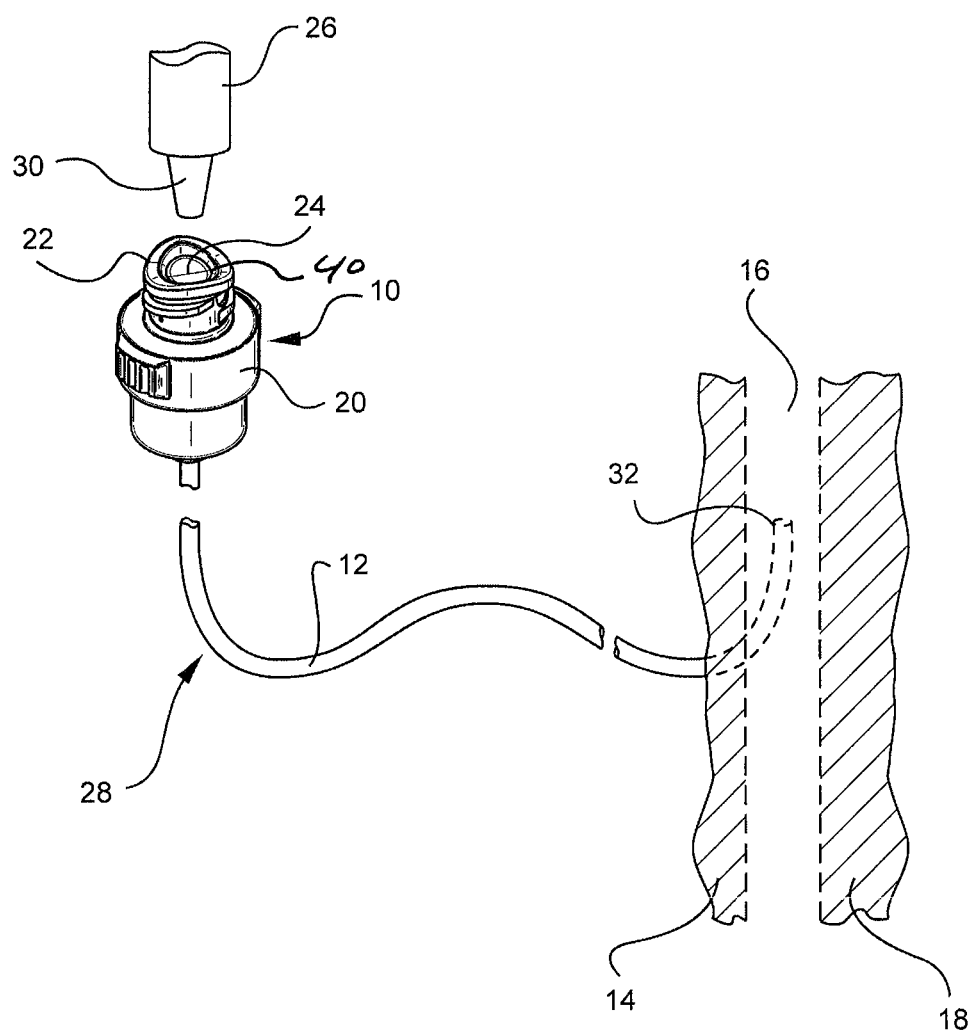

ANTIMICROBIAL LUBRICANT COMPOSITIONS

RELATED APPLICATIONS

This application claims priority to U.S. provisional patent application No. 61/118,988, filed Dec. 1, 2008, entitled "Antimicrobial Compositions and Methods for Medical Product Use," which application is incorporated herein by this reference.

BACKGROUND OF THE INVENTION

The present invention relates to antimicrobial compositions and methods for use of those compositions in various medical applications. One of the major challenges of modern medical treatment is control of infection and the spread of microbial organisms.

One area where this challenge is constantly presented is in infusion therapy of various types. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access, to many centimeters for central access and may include devices such as peripherally inserted central catheters (PICC). The catheter may be inserted transcutaneously or may be surgically implanted beneath the patient's skin. The catheter, or any other vascular access device attached thereto, may have a single lumen or multiple lumens for infusion of many fluids simultaneously.

The vascular access device commonly includes a Luer adapter to which other medical devices may be attached. For example, an administration set may be attached to a vascular access device at one end and an intravenous (IV) bag at the other. The administration set is a fluid conduit for the continuous infusion of fluids and pharmaceuticals. Commonly, an IV access device is a vascular access device that may be attached to another vascular access device, closes the vascular access device, and allows for intermittent infusion or injection of fluids and pharmaceuticals. An IV access device may include a housing and a septum for closing the system. The septum may be opened with a blunt cannula or a male Luer of a medical device.

When the septum of a vascular access device fails to operate properly or has inadequate design features, certain complications may occur. Complications associated with infusion therapy may cause significant morbidity and even mortality. One significant complication is catheter related blood stream infection (CRBSI). An estimate of 250,000-400,000 cases of central venous catheter (CVC) associated BSIs occur annually in US hospitals.

A vascular access device may serve as a nidus of infection, resulting in a disseminated BSI (blood stream infection). This may be caused by failure to regularly flush the device, a non-sterile insertion technique, or by pathogens that enter the fluid flow path through either end of the path subsequent to catheter insertion. When a vascular access device is contaminated, pathogens adhere to the vascular access device, colonize, and form a biofilm. The biofilm is resistant to most biocidal agents and provides a replenishing source for pathogens to enter a patient's bloodstream and cause a BSI. Thus, devices with antimicrobial properties are needed.

One approach to preventing biofilm formation and patient infection is to provide an antimicrobial coating on various medical devices and components. Many medical devices are made with either metallic or polymeric materials. These materials usually have a high coefficient of friction. A low molecular weight material or liquid with a low coefficient of friction is usually compounded into the bulk of the materials or coated onto the surface of the substrates to help the functionality of the devices.

Over the last 35 years, it has been common practice to use a thermoplastic polyurethane solution as the carrier for antimicrobial coatings. The solvent is usually tetrahydrofuran (THF), dimethylformamide (DMF), or a blend of both. Because THF can be oxidized very quickly and tends to be very explosive, an expensive explosion-proof coating facility is necessary. These harsh solvents also attack many of the polymeric materials commonly used, including polyurethane, silicone, polyisoprene, butyl rubber polycarbonate, rigid polyurethane, rigid polyvinyl chloride, acrylics, and styrene-butadiene rubber (SBR). Therefore, medical devices made with these materials can become distorted over time and/or form microcracks on their surfaces. Another issue with this type of coating is that it takes almost 24 hours for the solvent to be completely heat evaporated. Accordingly, conventional technology has persistent problems with processing, performance, and cost.

Another limitation to the use of such devices is the general availability of suitable antimicrobial agents for use in controlling microbial growth. One of the most commonly used antimicrobial agents used in medical devices is silver. Silver salts and silver element are well known antimicrobial agents in both the medical surgical industry and general industries. They are usually incorporated into the polymeric bulk material or coated onto the surface of the medical devices by plasma, heat evaporation, electroplating, or by conventional solvent coating technologies. These technologies are tedious, expensive, and not environmentally friendly.

In addition, the performance of silver coated medical devices is mediocre at best. For example, it can take up to eight (8) hours before the silver ion, ionized from the silver salts or silver element, to reach efficacy as an antimicrobial agent. As a result, substantial microbial activity can occur prior to the silver coating even becoming effective. Furthermore, the silver compound or silver element has an unpleasant color, from dark amber to black.

Vascular access devices of this type may require, or benefit from the use of, a lubricant. A lubricant can be applied to the moveable parts of the device in order to facilitate actuation of the septum. However, with conventional lubricants, bacteria and other microorganisms may also reside in the lubricant. Conventional lubricants are not intended to prevent or significantly inhibit microbial growth and propagation. Indeed, conventional lubricants may play a role in the spread of microbial agents.

Accordingly, there is a need in the art for improved methods for providing antimicrobial capability to medical devices of various types, and particularly devices related to infusion therapy. Specifically, there is a need for an effective antimicrobial lubricant that can be used in connection with various types of medical devices. There is a need for a lubricant that aids in preventing microbial propagation and may be useful and effective in killing microbial agents on contact.

BRIEF SUMMARY OF THE INVENTION

The present invention has been developed in response to problems and needs in the art that have not yet been fully resolved by currently available antimicrobial compositions and methods. Thus, these compositions and methods are developed to reduce complications, such as the risk and occurrence of CRBSIs, by providing improved antimicrobial compositions and methods for use in conjunction with medical devices.

As mentioned above, certain types of medical devices require a lubricant in order to operate smoothly and effectively. If a device is repeatedly moved from one position to another, a lubricant is often employed. One example of this type of device is an IV access device of the type described above. These devices may, for example, have an internal septum that is repeatedly actuated. For example, the septum may be opened with a blunt cannula or a male Luer of a medical device. Once the cannula or Luer is removed, the septum must move back to its original closed configuration. Therefore, lubricants may be employed in order to facilitate smooth and reliable actuation of the device.

As a result, in one aspect the invention comprises lubricants that have antimicrobial properties, and are intended for use on medical devices. The lubricants of the present invention are particularly useful on intravascular access devices like needleless valves of the type described above. The medical devices themselves are comprised of polymeric substrates, especially elastomeric substrates (e.g. polyurethane, silicone, polyisoprene, butyl rubber). Their surfaces are coated with the lubricant, which contains antimicrobial agents uniformly distributed throughout its matrix. The antimicrobial agents are able to diffuse through the matrix and kill microscopic organisms that come in contact with the lubricant surface.

The formulations of the lubricant in this invention are comprised of a mixture or combination of one or more oil lubricants, optional rheological modifiers, and antimicrobial agents. In the mixture, the nano- or micro-sized particles of the antimicrobial agents are uniformly and permanently distributed throughout the lubricant matrix. The rheological modifiers are used as needed to control the properties of the resulting mixture. The lubricant formulation is solventless. Thus, the problems mentioned above when using harsh solvents such as THF and DMF are avoided.

The oil lubricant can be polydimethyl siloxane, polytrifluoropropylmethyl siloxane, or a copolymer of dimethylsiloxane and trifluoropropylmethylsiloxane. It is preferred that these materials have a viscosity less than 50,000 cps.

As mentioned above, in some embodiments it is preferable to add a rheological modifier to the materials listed above. Examples of such rheological modifiers including organic clay, castor wax, polyamide wax, polyurethane, and fumed silica. Any rheology modifier which is compatible with the lubricant and the antimicrobial agents is acceptable for use in the composition.

An antimicrobial agent is also added to the lubricant composition. The antimicrobial agent may be any agent which is compatible with the other components of the lubricant formulation. In addition, it is preferred that the antimicrobial agent overcome certain limitations of the prior art. In some embodiments, the antimicrobial agents may be selected from the group consisting of aldehydes, anilides, biguanides, silver element, or its compound, bis-phenols, quaternary ammonium compounds, cetyl pyridium chloride, cetrimide, alexidine, chlorhexidine diacetate, benzalkonium chloride, and o-phthalaldehyde.

In some embodiments of the invention, these components are mixed uniformly in order to produce the inventive antimicrobial lubricant. Thus, manufacturing and processing is relatively easy and inexpensive. Furthermore, since the antimicrobial agents are uniformly distributed in the lubricant matrix, they gradually diffuse out of the matrix. This results in control of microbiological agents and specifically in killing the microbes that come in contact with the lubricant surface.

Thus, the present invention provides antimicrobial lubricants that are effective when used in connection with medical devices. The lubricant provides effective lubrication of the medical device, while at the same time providing significant antimicrobial properties. The lubricant is formulated without the use of harsh solvents or other chemical agents which would complicate processing and formulation. In addition, the formulation is effective as an antimicrobial since the antimicrobial agent is readily available to diffuse through the lubricant and reach the site of microbial activity.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawing. This drawing depicts only a typical embodiment of the invention and is not therefore to be considered to limit the scope of the invention.

FIG. 1 is a perspective view of an embodiment of a catheter assembly in accordance with the present invention.

DETAILED DESCRIPTION OF THE INVENTION

Referring now to FIG. 1, a vascular access device (also referred to as an extravascular device, intravenous access device, access port, and/or any device attached to or functioning with an extravascular system) 10 is used to introduce a substance via a catheter 12 across the skin 14 and into a blood vessel 16 of a patient 18. The vascular access device 10 includes a body 20 with a lumen and a septum 22 placed within the lumen. The septum 22 has a slit 24 through which a separate extravascular device 26, such as a syringe, may introduce a substance into the vascular access device 10.

The device 10 also includes an antimicrobial lubricant 40 applied to the septum 22 in order to facilitate operation of the device and to inhibit the growth and propagation of microbial organisms. The lubricant helps prevent microbial pathogens within the vascular access device 10, including the catheter 12 and the end 32 of the catheter 12, and/or the extravascular system 28 to which the vascular access device 10 is connected. The lubricant contacts microbial pathogens as they enter the septum 22 to decrease the incidence of blood stream infections in patients to whom the vascular access device 10 or any other device on an extravascular system 28 is attached.

A pathogen may enter the device 10 or system 28 in any of a number of ways. For example, a pathogen may reside within the device 10 or system 28 prior to first use. A pathogen may also be introduced into the device 10 from the external surface of the device, the external surface of a separate device 26, and/or the surrounding environment when a structure such as a tip 30 of the separate device 26 is inserted into the device 10 through the slit 24 of the septum 22. A pathogen may be introduced within fluid that is infused into the system from a separate device 26. Finally, a pathogen may be introduced from a blood vessel 16 into the system 28 by entering through the end 32 of the catheter 12 during a blood draw or a period of blood reflux when the device 10 is in use. Microbial pathogens include any agent that causes a disease or otherwise harms or has the potential to harm a patient if received into the vascular system of that patient, including a pathogen, bacterium, parasite, microbe, biofilm, fungus, virus, protein feeding a pathogen, protozoan, and/or other harmful microorganisms and/or agents and products thereof.

As discussed above, the antimicrobial lubricant of the present invention may be comprised of an oil lubricant; a rheological modifier; and an antimicrobial agent. The oil lubricant is any material that is capable of lubricating the selected medical device to which it is applied. For many of the types of devices described herein, the oil lubricant is generally selected from the group consisting of polydimethyl siloxane, polytrifluoropropylmethyl siloxane, and a copolymer of dimethylsiloxane and trifluoropropylmethylsiloxane. In some preferred embodiments, the oil lubricant is a copolymer of dimethylsiloxane and trifluoropropylmethylsiloxane. In some embodiments, the oil lubricant has a viscosity of 50,000 cps or less and preferably 1000 cps or less.

The antimicrobial lubricant composition may also comprise one or more rheological modifiers. In certain preferred embodiments, the rheological modifier is added in the amount of from about 0.2 to about 30 parts by weight in 100 parts by weight of the oil lubricant. In other preferred embodiments the lubricant composition may comprise rheological modifier in the amount of from about 0.2 to about 20 parts by weight of the rheological modifiers in 100 parts by weight of the oil lubricant. In other preferred embodiments, the lubricant composition may contain rheological modifier in the amount of from about 0.2 to about 10 parts by weight of the rheological modifiers in 100 parts by weight of the oil lubricant.

As discussed above, in certain embodiments, the rheological modifier is selected from the group consisting of organic clay, castor wax, polyamide wax, polyurethane, and fumed silica. In certain instances fumed silica may be preferred. However, other rheological modifiers may be used as desired.

The composition may also contain one or more antimicrobial agent. The antimicrobial agent is selected such that it is compatible with the other components of the antimicrobial lubricant composition. Also, the antimicrobial agent is compatible with the medical device to which the antimicrobial lubricant composition is applied.

Generally, the antimicrobial agent is present in the antimicrobial lubricant composition in the amount of from about 0.5 to about 50 parts by weight in 100 parts of the oil lubricant. In certain other embodiments the antimicrobial agent may be present in the amount of from about 0.5 to about 30 parts by weight in 100 parts by weight of the oil lubricant. In certain other embodiments, the antimicrobial agent may be present in the amount of from about 0.5 to about 20 parts by weight in 100 parts by weight of the oil lubricant.

Acceptable antimicrobial agents may include, but are not limited to, aldehydes, anilides, biguanides, bis-phenols, and quaternary ammonium compounds. In certain embodiments, the antimicrobial agent may be selected from the group consisting of cetyl pyridium chloride, cetrimide, alexidine, chlorhexidine diacetate, benzalkonium chloride, and o-phthalaldehyde.

In summary, in certain embodiments the antimicrobial lubricant composition may be formulated from the following: a lubricant selected from the group consisting of polydimethyl siloxane, polytrifluoropropylmethyl siloxane, and a copolymer of dimethylsiloxane and trifluoropropylmethylsiloxane; a rheological modifier selected from the group consisting of organic clay, castor wax, polyamide wax, polyurethane, and fumed silica; and an antimicrobial agent selected from the group consisting of cetyl pyridium chloride, cetrimide, alexidine, chlorhexidine diacetate, benzalkonium chloride, and o-phthalaldehyde.

EXAMPLES

Example 1

Table 1 illustrates the contact kill and zone of inhibition of different lubricant formulations. As shown in Table 1, the silver element (10) and silver compound (3, 4 and 5) all have relatively low contact kill until 8 hours later. Cetyl pyridium chloride, cetrimide, alexidine, chlorhexidine diacetate and benzalkonium chloride all have significant contact kill within 1 minute.

TABLE 1

The Contact Kill (% kill) and Zone of Inhibition (mm) of Different Lubricant Formulations[1].

| Sample #[2] | Contact Kill (% Kill)[4] | | | | | | | | | Zone of Inhibition (mm) | | |
|---|---|---|---|---|---|---|---|---|---|---|---|---|
| | S. epidermidis[3] | | | P. aeruginosa | | | C. albicans | | | | | |
| | 1 min. | 1 hr. | 8 hr. | 1 min. | 1 hr. | 8 hr. | 1 min | 1 hr. | 8 hr. | S. epider | P. aerug | C. albicans |
| 1 | 100 | ND | ND | 98.2 | ND | ND | 64.4 | 100 | ND | 20.0 | 9.0 | 20.0 |
| 2 | 100 | ND | ND | 100 | ND | ND | 100 | ND | ND | 11.0 | + | 14.5 |
| 3 | 0.0 | 26.0 | 100 | 0.0 | 49.7 | 100 | 0.0 | 38.3 | 94.6 | 7.0 | 6.0 | 8.0 |
| 4 | 0.0 | 8.0 | 100 | 9.7 | 36.1 | 100 | 0.0 | 22.2 | 75.5 | 8.0 | 8.8 | 10.8 |
| 5 | 0.0 | 20.0 | 100 | 96.0 | 91.2 | 100 | 0.0 | 74.1 | 90.0 | 10.5 | 9.0 | 10.8 |
| 6 | 100 | ND | ND | 100 | ND | ND | 100 | ND | ND | 30.5 | 7.0 | 21.8 |
| 7 | 100 | ND | ND | 100 | ND | ND | 100 | ND | ND | 14.5 | 0.0 | 13.0 |
| 8 | 0.0 | 100 | ND | 100 | ND | ND | 100 | ND | ND | 27.0 | 0.0 | 21.3 |

TABLE 1-continued

| | | | | | | | | | | | | |
|---|---|---|---|---|---|---|---|---|---|---|---|---|
| 9 | 0.0 | 100 | ND | 21.2 | 100 | ND | 64.4 | 100 | ND | 20.5 | 0.0 | 8.3 |
| 10 | 0.0 | 0.0 | 78.9 | 0.0 | 37.4 | 27.8 | 0.0 | 3.7 | 30.0 | 0.0 | 0.0 | + |

Note 1. Lubricant formulations: Med.-460 (350 cps)
Rheological modifier: M-5 Antimicrobial agent(s)
Note 2. Antimicrobial agent(s)
Samples #   1. hlorhexidine diacetate
            2. Alexidine
            3 Silver sulfadiazine
            4. Silver acetate
            5. Silver citrate hydrate
            6. Cetrimide
            7. Cetyl pyridium chloride
            8. Benzalknonium chloride
            9. o-phthalaldehyde
            10. Silver element
Note 3. Microbe
S. epider: Staphylococcus epidermidis
P. aerug: Pseudomonas aeruginosa
C. albicans: Candida albicans
Note 4. ND = no data, all microbes have been killed.

Example 2

Based on initial test data, one preferred embodiment of the lubricant invention may be formulated as follows:
1. Lubricant(s)—Med-460, 350 cps from Nusil Silicone Technology (Carpinteria, Calif.)
2. Rheology modifier(s)—Fumed silica from Cabot Corporation (Tuscola, Ill.)
3. Antimicrobial agent(s)—Cetyl pyridium chloride, cetrimide, alexidine, chlorhexidine diacetate or benzalkonium chloride.

Example 3

Table 2 illustrates the contact kill and zone of inhibition of different lubricant compositions. Samples 1-5 included the lubricant Med.-360 which is comprised of polydimethyl siloxane with a viscosity of 350 cps. The antimicrobial agent was varied as follows:
1. chlorhexidine diacetate
2. cetrimide
3. cetyl pyridium chloride
4. benzalkonium chloride
5. o-phthalaldehyde Example 4

Table 3 illustrates the contact kill and zone of inhibition of different lubricant compositions. Samples 6-10 lubricant Med.-360 which is comprised of polydimethyl siloxane with a viscosity of 1000 cps. The antimicrobial agent was varied as follows:
6. chlorhexidine diacetate
7. cetrimide
8. cetyl pyridium chloride
9. benzalkonium chloride
10. o-phthalaldehyde

TABLE 2

The Contact Kill (% kill) and Zone of Inhibition (mm) of Different Lubricant Formulations[1].

| Sample #[2] | Contact Kill (% Kill)[4] | | | | | | | | | Zone of Inhibition (mm) | | |
|---|---|---|---|---|---|---|---|---|---|---|---|---|
| | S. epidermidis[3] | | | P. aeruginosa | | | C. albicans | | | | | |
| | 1 min. | 1 hr. | 8 hr. | 1 min. | 1 hr. | 8 hr. | 1 min | 1 hr. | 8 hr. | S. epider | P. aerug | C. albicans |
| 1 | 93.6 | ND | ND | 97.6 | ND | ND | 50.0 | 100 | ND | 19.0 | 6.5 | 13.0 |
| 2 | 100 | ND | ND | 100 | ND | ND | 100 | ND | ND | 31.5 | 20.5 | 21.0 |
| 3 | 100 | ND | ND | 100 | ND | ND | 100 | ND | ND | 19.5 | 17.0 | 14.0 |
| 4 | 100 | ND | ND | 100 | ND | ND | 100 | ND | ND | 28.0 | 16.5 | 23.0 |
| 5 | 98.2 | ND | ND | 63.4 | 100 | ND | 100 | ND | ND | 30.0 | 17.0 | 14.0 |

TABLE 3

The Contact Kill (% kill) and Zone of Inhibition (mm) of Different Lubricant Formulations[1].

| Sample #[2] | S. epidermidis[3] Contact Kill (% Kill)[4] | | | P. aeruginosa | | | C. albicans | | | Zone of Inhibition (mm) | | |
|---|---|---|---|---|---|---|---|---|---|---|---|---|
| | 1 min. | 1 hr. | 8 hr. | 1 min. | 1 hr. | 8 hr. | 1 min | 1 hr. | 8 hr. | S. epider | P. aerug | C. albicans |
| 6 | 100 | ND | ND | 100 | ND | ND | 37.0 | 100 | ND | 18.5 | 6.5 | 11.5 |
| 7 | 100 | ND | ND | 100 | ND | ND | 100 | ND | ND | 28.5 | 17.0 | 19.5 |
| 8 | 100 | ND | ND | 100 | ND | ND | 100 | ND | ND | 18.5 | 0 | 15.0 |
| 9 | 100 | ND | ND | 100 | ND | ND | 100 | ND | ND | 28.5 | "+" | 27.5 |
| 10 | 99.1 | ND | ND | 87.8 | ND | ND | 100 | ND | ND | 17.0 | 0 | 15.5 |

Example 5

Table 4 illustrates the contact kill and zone of inhibition of different lubricant compositions. Samples 11-15 included the lubricant Med.-400 which is comprised of polytrifluoropropylmethyl siloxane with a viscosity of 350 cps. The antimicrobial agent was varied as follows:
11. chlorhexidine diacetate
12. cetrimide
13. cetyl pyridium chloride
14. benzalkonium chloride
15. o-phthalaldehyde

TABLE 4

The Contact Kill (% kill) and Zone of Inhibition (mm) of Different Lubricant Formulations[1].

| Sample #[2] | S. epidermidis[3] Contact Kill (% Kill)[4] | | | P. aeruginosa | | | C. albicans | | | Zone of Inhibition (mm) | | |
|---|---|---|---|---|---|---|---|---|---|---|---|---|
| | 1 min. | 1 hr. | 8 hr. | 1 min. | 1 hr. | 8 hr. | 1 min | 1 hr. | 8 hr. | S. epider | P. aerug | C. albicans |
| 11 | 100 | ND | ND | 100 | ND | ND | 100 | ND | ND | 18.0 | "+" | 12.5 |
| 12 | 100 | ND | ND | 100 | ND | ND | 100 | ND | ND | 33.5 | 0 | 23.0 |
| 13 | 100 | ND | ND | 100 | ND | ND | 100 | ND | ND | 19.5 | 0 | 15.0 |
| 14 | 89.1 | 100 | ND | 7.32 | 100 | ND | 6.52 | 100 | ND | 17.0 | 0 | 15.5 |
| 15 | 100 | ND | ND | 100 | ND | ND | 100 | ND | ND | 29.0 | 0 | 15.5 |

Example 6

Table 5 illustrates the contact kill and zone of inhibition of different lubricant compositions. Samples 16-20 included the lubricant Med.-400 which is comprised of polytrifluoropropylmethyl siloxane with a viscosity of 1000 cps. The antimicrobial agent was varied as follows:
16. chlorhexidine diacetate
17. cetrimide
18. cetyl pyridium chloride
19. benzalkonium chloride
20. o-phthalaldehyde

TABLE 5

The Contact Kill (% kill) and Zone of Inhibition (mm) of Different Lubricant Formulations[1].

| Sample #[2] | S. epidermidis[3] Contact Kill (% Kill)[4] | | | P. aeruginosa | | | C. albicans | | | Zone of Inhibition (mm) | | |
|---|---|---|---|---|---|---|---|---|---|---|---|---|
| | 1 min. | 1 hr. | 8 hr. | 1 min. | 1 hr. | 8 hr. | 1 min | 1 hr. | 8 hr. | S. epider | P. aerug | C. albicans |
| 16 | 100 | ND | ND | 100 | ND | ND | 100 | ND | ND | "+" | "+" | 10.0 |
| 17 | 100 | ND | ND | 100 | ND | ND | 100 | ND | ND | "+" | "+" | 24.5 |

TABLE 5-continued

The Contact Kill (% kill) and Zone of Inhibition (mm) of Different Lubricant Formulations[1].

| Sample #[2] | Contact Kill (% Kill)[4] | | | | | | | | | Zone of Inhibition (mm) | | |
|---|---|---|---|---|---|---|---|---|---|---|---|---|
| | S. epidermidis[3] | | | P. aeruginosa | | | C. albicans | | | | | |
| | 1 min. | 1 hr. | 8 hr. | 1 min. | 1 hr. | 8 hr. | 1 min | 1 hr. | 8 hr. | S. epider | P. aerug | C. albicans |
| 18 | 100 | ND | ND | 100 | ND | ND | 100 | ND | ND | "+" | "+" | 14.0 |
| 19 | 100 | ND | ND | 100 | ND | ND | 100 | ND | ND | "+" | "+" | 32.0 |
| 20 | 91.8 | ND | ND | 80.5 | 100 | ND | 100 | ND | ND | 23.0 | 0 | 9.0 |

Example 7

Table 6 illustrates the contact kill and zone of inhibition of different lubricant compositions. Samples 21-25 included the lubricant Med.-420 which is comprised of a copolymer of dimethylsiloxane and trifluoropropylmethylsiloxane with a viscosity of 350 cps. The antimicrobial agent was varied as follows:
21. chlorhexidine diacetate
22. cetrimide
23. cetyl pyridium chloride
24. benzalkonium chloride
25. o-phthalaldehyde

TABLE 6

The Contact Kill (% kill) and Zone of Inhibition (mm) of Different Lubricant Formulations[1].

| Sample #[2] | Contact Kill (% Kill)[4] | | | | | | | | | Zone of Inhibition (mm) | | |
|---|---|---|---|---|---|---|---|---|---|---|---|---|
| | S. epidermidis[3] | | | P. aeruginosa | | | C. albicans | | | | | |
| | 1 min. | 1 hr. | 8 hr. | 1 min. | 1 hr. | 8 hr. | 1 min | 1 hr. | 8 hr. | S. epider | P. aerug | C. albicans |
| 21 | 100 | ND | ND | 90.2 | ND | ND | 23.9 | 100 | ND | 22.0 | "+" | 10.5 |
| 22 | 100 | ND | ND | 100 | ND | ND | 100 | ND | ND | 40.0 | "+" | 27.5 |
| 23 | 100 | ND | ND | 100 | ND | ND | 100 | ND | ND | 40.0 | 0 | 19.5 |
| 24 | 100 | ND | ND | 100 | ND | ND | 100 | ND | ND | 40.0 | "+" | 31.0 |
| 25 | 100 | ND | ND | 95.1 | ND | ND | 100 | ND | ND | 40.0 | 0 | 16 |

Example 8

Table 7 illustrates the contact kill and zone of inhibition of different lubricant compositions. Samples 26-30 included the lubricant Med.-420 which is comprised of a copolymer of dimethylsiloxane and trifluoropropylmethylsiloxane with a viscosity of 1000 cps. The antimicrobial agent was varied as follows:
26. chlorhexidine diacetate
27. cetrimide
28. cetyl pyridium chloride
29. benzalkonium chloride
30. o-phthalaldehyde

TABLE 7

The Contact Kill (% kill) and Zone of Inhibition (mm) of Different Lubricant Formulations[1].

| Sample #[2] | Contact Kill (% Kill)[4] | | | | | | | | | Zone of Inhibition (mm) | | |
|---|---|---|---|---|---|---|---|---|---|---|---|---|
| | S. epidermidis[3] | | | P. aeruginosa | | | C. albicans | | | | | |
| | 1 min. | 1 hr. | 8 hr. | 1 min. | 1 hr. | 8 hr. | 1 min | 1 hr. | 8 hr. | S. epider | P. aerug | C. albicans |
| 26 | 100 | ND | ND | 97.6 | ND | ND | 34.8 | 100 | ND | 40.0 | 9.0 | 17.0 |
| 27 | 100 | ND | ND | 100 | ND | ND | 100 | ND | ND | 40.0 | "+" | 27.5 |

TABLE 7-continued

The Contact Kill (% kill) and Zone of Inhibition (mm) of Different Lubricant Formulations[1].

| Sample #[2] | Contact Kill (% Kill)[4] | | | | | | | | | Zone of Inhibition (mm) | | |
|---|---|---|---|---|---|---|---|---|---|---|---|---|
| | S. epidermidis[3] | | | P. aeruginosa | | | C. albicans | | | | | |
| | 1 min. | 1 hr. | 8 hr. | 1 min. | 1 hr. | 8 hr. | 1 min | 1 hr. | 8 hr. | S. epider | P. aerug | C. albicans |
| 28 | 100 | ND | ND | 100 | ND | ND | 100 | ND | ND | 40.0 | 0 | 22.0 |
| 29 | 100 | ND | ND | 100 | ND | ND | 100 | ND | ND | 38.5 | "+" | 32.0 |
| 30 | 100 | ND | ND | 92.7 | ND | ND | 97.8 | ND | ND | 40.0 | 0 | 10.5 |

Example 9

Table 8 illustrates the contact kill and zone of inhibition of different lubricant compositions. Samples 31-35 included the lubricant Med.-460 which is comprised of a copolymer of dimethylsiloxane and trifluoropropylmethylsiloxane with a viscosity of 1000 cps. The antimicrobial agent was varied as follows:
31. chlorhexidine diacetate
32. cetrimide
33. cetyl pyridium chloride
34. benzalkonium chloride
35. o-phthalaldehyde

TABLE 8

The Contact Kill (% Kill) and Zone of Inhibition (mm) of Different Lubricant Formulations[1].

| Sample #[2] | Contact Kill (% Kill)[4] | | | | | | | | | Zone of Inhibition (mm) | | |
|---|---|---|---|---|---|---|---|---|---|---|---|---|
| | S. epidermidis[3] | | | P. aeruginosa | | | C. albicans | | | | | |
| | 1 min. | 1 hr. | 8 hr. | 1 min. | 1 hr. | 8 hr. | 1 min | 1 hr. | 8 hr. | S. epider | P. aerug | C. albicans |
| 31 | 100 | ND | ND | 91.2 | 100 | ND | 0 | 100 | ND | 21.5 | 8.0 | 15.0 |
| 32 | 100 | ND | ND | 100 | ND | ND | 100 | ND | ND | 29.5 | 16.0 | 26.5 |
| 33 | 100 | ND | ND | 100 | ND | ND | 100 | ND | ND | 21.0 | 0 | 19.5 |
| 34 | 100 | ND | ND | 100 | ND | ND | 100 | ND | ND | 38.5 | 10.5 | 39.0 |
| 35 | 100 | ND | ND | 100 | ND | ND | 100 | ND | ND | 30.0 | 0 | 19.5 |

It will also be appreciated that lubricant with a viscosity of less than 50,000 cps is generally preferred. Such lubricants may be as follows: polydimethyl siloxane with a viscosity less than 50,000 cps; trifluoropropyl copolymer polysiloxane with a viscosity less than 50,000 cps.; and a copolymer of dimethylsiloxane and trifluoropropylmethylsiloxane with a viscosity less than 50,000 cps.

As mentioned above, the rheological modifiers can be organic clay, castor wax, polyamide wax, polyurethane, fumed silica, etc. The quantity of the modifier should be less than 30 parts by weight in 100 parts by weight of the lubricant, preferably less than 20 parts by weight, and most preferably between 0.2 to 10 parts by weight in 100 parts of the lubricant.

The antimicrobial agents can be aldehydes, anilides, biguanides, silver element or its compound, bis-phenols, and quaternary ammonium compounds for the formulations. In some preferred embodiments the agents could be cetyl pyridium chloride, cetrimide, and benzalkonium chloride, alexidine, or chlorhexidine diacetate. The quantity of the agent in the formulation should be less than 50 parts by weight in 100 parts by weight of the lubricant, preferably less than 30 parts by weight, and most preferably between 0.5 to 20 parts by weight in 100 parts by weight of the lubricant.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device comprising:
    a medical device having a surface coated with an antimicrobial composition, the antimicrobial composition comprising an oil lubricant;
    a rheological modifier selected from the group consisting of organic clay, castor wax, polyamide wax, polyurethane, and fumed silica; and
    an antimicrobial agent selected from the group consisting of aldehydes, anilides, biguanides, bis-phenols, quaternary ammonium compounds, cetyl pyridium chloride, cetrimide, alexidine, chlorhexidine diacetate, benzalkonium chloride, and o-phthalaldehyde.

2. The medical device of claim 1 wherein the antimicrobial agent is selected from the group consisting of aldehydes, anilides, biguanides, silver, silver compounds, bis-phenols, and quaternary ammonium compounds.

3. The medical device of claim 1 wherein the antimicrobial agent is selected from the group consisting of cetyl pyridium chloride, cetrimide, alexidine, chlorhexidine diacetate, benzalkonium chloride, and o-phthalaldehyde.

4. The medical device of claim 1 wherein the lubricant is selected from the group consisting of polydimethyl siloxane, polytrifluoropropylmethyl siloxane, and a copolymer of dimethylsiloxane and trifluoropropylmethylsiloxane.

5. The medical device of claim 1 wherein the lubricant is a copolymer of dimethylsiloxane and trifluoropropylmethylsiloxane.

6. The medical device of claim 1 wherein the lubricant has a viscosity of 50,000 cps or less.

7. The medical device of claim 1 wherein the composition comprises rheological modifier in the amount of from about 0.2 parts by weight to about 30 parts by weight in 100 parts by weight of the oil lubricant.

8. The medical device of claim 1 wherein the composition comprises rheological modifier in the amount of from about 0.2 parts by weight to about 20 parts by weight in 100 parts by weight of the oil lubricant.

9. The medical device of claim 1 wherein the composition comprises rheological modifier in the amount of from about 0.2 parts by weight to about 10 parts by weight in 100 parts by weight of the oil lubricant.

10. The medical device of claim 1 wherein the rheological modifier is fumed silica.

11. The medical device of claim 1 wherein the composition comprises antimicrobial agent in the amount of from about 0.5 parts by weight to about 50 parts by weight in 100 parts by weight of the oil lubricant.

12. The medical device of claim 1 wherein the composition comprises antimicrobial agent in the amount of from about 0.5 parts by weight to about 30 parts by weight in 100 parts by weight of the oil lubricant.

13. The medical device of claim 1 wherein the composition comprises antimicrobial agent in the amount of from about 0.5 parts by weight to about 20 parts by weight in 100 parts by weight of the oil lubricant.

14. A lubricant for coating a medical device, comprising:
an oil lubricant selected from the group consisting of polydimethyl siloxane, polytrifluoropropylmethyl siloxane, and a copolymer of dimethylsiloxane and trifluoropropylmethylsiloxane;
a rheological modifier selected from the group consisting of organic clay, castor wax, polyamide wax, polyurethane, and fumed silica; and
an antimicrobial agent selected from the group consisting of cetyl pyridium chloride, cetrimide, alexidine, chlorhexidine diacetate, benzalkonium chloride, and o-phthalaldehyde
wherein the lubricant is applied to a surface of a medical device, the surface being capable of being placed in fluid communication with the vasculature of a patient during normal operation of the device.

15. The lubricant of claim 14 wherein the composition comprises rheological modifier in the amount of from about 0.2 to about 30 parts by weight in 100 parts by weight of the oil lubricant.

16. The lubricant of claim 14 wherein the composition comprises antimicrobial agent in the amount of from about 0.5 to about 50 parts by weight in about 100 parts by weight of the oil lubricant.

17. A lubricant for coating a medical device, comprising:
an oil lubricant comprising a copolymer of dimethylsiloxane and trifluoropropylmethylsiloxane;
a rheological modifier comprising fumed silica; and
an antimicrobial agent selected from the group consisting of cetyl pyridium chloride, cetrimide, alexidine, chlorhexidene diacetate, and benzalkonium chloride
wherein the lubricant is applied to a surface of a medical device, the surface being capable of being placed in fluid communication with the vasculature of a patient during normal operation of the device.

* * * * *